(12) United States Patent
Zimmermann et al.

(10) Patent No.: US 12,300,117 B1
(45) Date of Patent: May 13, 2025

(54) AUTO-INJECTOR DEMONSTRATION DEVICE

(71) Applicants: Todd F Zimmermann, Chapel Hill, NC (US); George M Mason, Southampton, NJ (US); Charles K Huang, New Taipei (TW); Ching Huang, New Taipei (TW); Darryl Chemel, British Columbia (CA); Zohour Hassan, Flemington, NJ (US); Harold Zimmermann, Riverton, NJ (US)

(72) Inventors: Todd F Zimmermann, Chapel Hill, NC (US); George M Mason, Southampton, NJ (US); Charles K Huang, New Taipei (TW); Ching Huang, New Taipei (TW); Darryl Chemel, British Columbia (CA); Zohour Hassan, Flemington, NJ (US); Harold Zimmermann, Riverton, NJ (US)

(73) Assignee: THE ARTCRAFT GROUP, INC., Moorestown, NJ (US)

( * ) Notice: Subject to any disclaimer, the term of this patent is extended or adjusted under 35 U.S.C. 154(b) by 0 days.

(21) Appl. No.: 19/052,590

(22) Filed: Feb. 13, 2025

Related U.S. Application Data (60) Provisional application No. 63/555,485, filed on Feb. 20, 2024.

(51) Int. Cl.
*G09B 23/28* (2006.01)
*A61M 5/32* (2006.01)

(52) U.S. Cl.
CPC .......... *G09B 23/285* (2013.01); *A61M 5/326* (2013.01)

(58) Field of Classification Search
None
See application file for complete search history.

(56) References Cited

U.S. PATENT DOCUMENTS

| 12,011,572 | B2 * | 6/2024 | Baker | ............... A61M 5/31585 |
| 2017/0069230 | A1 * | 3/2017 | Baker | .................. G09B 23/285 |
| 2017/0148354 | A1 * | 5/2017 | Baker | .................. A61M 5/326 |

* cited by examiner

*Primary Examiner* — James B Hull
(74) *Attorney, Agent, or Firm* — Stuart M. Goldstein (57) ABSTRACT

An auto-injector demonstration device for simulating the delivery of medication has an elongated body encompassing a needle guard member with locking slots circumscribing a transparent window member having stop elements. A plunger, electronically controlled by a transmission motor, has bump-out elements. In use, the needle guard member is pressed against the injection site to actuate the transmission motor. This moves the plunger through the window member to simulate the medication delivery. When the plunger reaches its terminal position, the bump-out elements compel the stop elements on the window member outward. When the user allows the needle guard member to ease back into the original extended position, the stop elements will engage with the locking slots through the needle guard member to lock and prevent the needle guard from retracting into the window member.

6 Claims, 9 Drawing Sheets

AUTO-INJECTOR DEMONSTRATION DEVICE

RELATED APPLICATION

This application claims the benefit of application Ser. No. 63/555,485, filed on Feb. 20, 2024.

FIELD OF THE INVENTION

The present invention relates to the field of demonstration and training devices, particularly to a more precise and controllable device to help users learn how to successfully use the category of self-injection medical devices known as auto-injectors.

BACKGROUND OF THE INVENTION

The category of self-injection devices known as auto-injectors has gained tremendous popularity in recent years due to their effectiveness in delivering both emergency and maintenance medications. Auto-injectors enable emergency users, patients and healthcare providers to deliver a dose of medication without seeing a needle, which is hidden from view by a needle shield, or having to bear responsibility for needle depth as they inject into the recommended area of the body. Commercial auto-injectors can typically be used only once and contain both medication and a needle, so they are not appropriate for non-therapeutic user training programs intended to develop proper technique.

Demonstration and training devices, however, are made to allow the user to practice the steps that will be necessary for using the commercial auto-injector, but without the presence of a needle or medication. In addition, demonstration and training devices are made to be resettable and reusable, with the goal that the device can be used for hundreds of accurate training sessions before being discarded.

Commercial auto-injectors typically use a spring-loaded medication delivery method, and most demonstration devices follow suit. The problem with this approach is that commercial auto-injectors must deliver a dose with precision one time, but a demonstration device must simulate delivery with precision dozens, scores or even hundreds of times. However, spring-loaded mechanisms of the size required to fit in an auto-injector demonstration device tend to degrade after repeated use, producing an inaccurate and potentially confusing training experience for the user.

Another shortfall of the existing mechanical demonstration devices is that they fail to accurately reproduce the sounds (such as 'clicks') that occur during successful use of the commercial device. This is due to the internal components being different than those of a one-time use commercial device. Furthermore, even if the demonstration device were able to simulate the commercial device sounds initially, the internal parts tend to wear with repeated demonstration use and thus continue to deviate from the sounds of the commercial device. In one common commercial auto-injector device, the click sounds are noted as the auditory clues that the medication delivery has begun (click) and completed (click.) The absence or inaccuracy of these auditory markers limits the training value of traditional spring-driven demonstration auto-injector devices.

Traditional demonstration auto-injector devices may require a cylindrical rod which is inserted into the device to reset the spring mechanism in preparation for the next demonstration. This rod mechanism is not present in the commercial auto-injector device and may confuse patients.

A final inadequacy of traditional demonstration auto-injectors is that they cannot count the number of demonstration cycles that the unit has completed in its lifetime. This prevents the user from celebrating heavy usage or taking corrective action for lack of usage, as well as failing to provide the user with a cycle count if the unit fails. This flaw has caused significant frustration with mechanical demonstration devices.

In summary, if the timing, feel, visualization and sounds the user experiences with the demonstration device are not representative of the commercial device they are preparing to use, the demonstration and training efforts will be less than optimal and could even provide negative value by increasing user anxiety about their ability to use the commercial auto-injector correctly.

SUMMARY OF THE INVENTION

It is thus the object of the present invention to provide a demonstration device that overcomes the disadvantages and limitations of prior devices and methods of operation.

It is the object of the present invention to provide an auto-injector demonstration device that allows for each demonstration to be electronically controlled and driven to ensure accurate simulation of the commercial experience that the demonstration device is intended to prepare the user to utilize successfully.

It is another object of the present invention to provide an auto-injector demonstration device which provides precise and consistent electronic representation of the sounds of the commercial auto-injector, reproduced via a piezoelectric speaker.

It is still another object of the present invention to provide an auto-injector demonstration device which includes the ability to detect correct or incorrect technique and provide feedback to the user and their trainer (e.g. notification of early lift-off before the simulated injection has been completed).

It is a further object of the present invention to provide an auto-injector demonstration device which includes the ability to reset the demonstration device electronically with a discreet button, eliminating the potentially confusing requirement for the user to insert a physical reset tool into the device.

It is still another object of the present invention to provide an auto-injector demonstration device which includes the ability to simulate medication delivery of different durations (e.g. some medications require a four second delivery cycle, while other medications require an eight second delivery cycle if using the same model of commercial auto-injector).

It is a further object of the present invention to provide an auto-injector demonstration device which has the ability to use a single device to show both a correctly prepared simulated injection (e.g. plunger moves at correct speed representing room temperature medication) and an incorrectly prepared simulated injection (plunger moves at slower speed because of viscous medication that has not been given enough time to acclimate to room temperature).

It is still another object of the present invention to provide an auto-injector demonstration device which has the ability to prompt the user to continue pressing the demonstration device against the simulated injection area for X seconds after the simulated dose has been completed to train the user to have a safety buffer, since sometimes the medication has not been delivered fully, even though the device 'click' may suggest that it has.

It is another object of the present invention to provide an auto-injector demonstration device which includes the ability to detect low battery or other impairments that will make it unlikely for the demonstration device to deliver an accurate demonstration experience, and to notify the user to prevent an inaccurate demonstration from being done.

It is a further object of the present invention to provide an auto-injector demonstration device which provides for wireless communication of demonstration status to a computing device to allow for multi-lingual software-based training instruction and data capture, enabling the user to build confidence that they have mastered the skills that will be necessary to use the commercial auto-injector device that will deliver their medication. This software could also be used to modify the timing and notification parameters of the demonstration device to allow for flexible training scenarios and product attribute testing.

It is still another object of the present invention to provide an auto-injector demonstration device which, upon resetting the device will report the total number of demonstration cycles to date, through a piezoelectric speaker, in human voice.

These and other objects are accomplished by an auto-injector demonstration device having an elongated body encompassing a needle guard member with locking slots circumscribing a transparent window member having stop elements. A plunger, electronically controlled by a transmission motor, has bump-out elements. To utilize the device to simulate the delivery of medication into an injection site, the needle guard member is pressed against the site until it reaches its fully compressed position. The transmission motor is actuated and begins to move the plunger through the window member at the desired rate of speed for the desired rotation to simulate medication delivery. When the plunger reaches its terminal position, the bump-out elements compel the stop elements on the window member outward in preparation for locking the needle guard member. When the user allows the needle guard member to ease back into the original extended position, the stop elements engage with the locking slots through the needle guard member to prevent it from retracting into the window member. The needle guard member will stay firmly in this locked/extended position until the user presses a reset button on the device in preparation for the next demonstration.

The novel features which are considered as characteristic of the invention are set forth in particular in the appended claims. The invention, itself, however, both as to its design, construction and use, together with additional features and advantages thereof, are best understood upon review of the following detailed description with reference to the accompanying drawings.

DETAILED DESCRIPTION OF THE INVENTION

Auto injector demonstration device 1 comprises elongated injector body 2 formed by bottom case 4 and top case 6, each case having exterior channel openings 8 and 10. Power switch 12 is located on bottom case 4 and top case 6. Reset button 14 is located at the end of device 1. USB-C charging port 16 is located on body 2 as well. Cap 19 is located at the bottom end of device 1.

Figure 1:
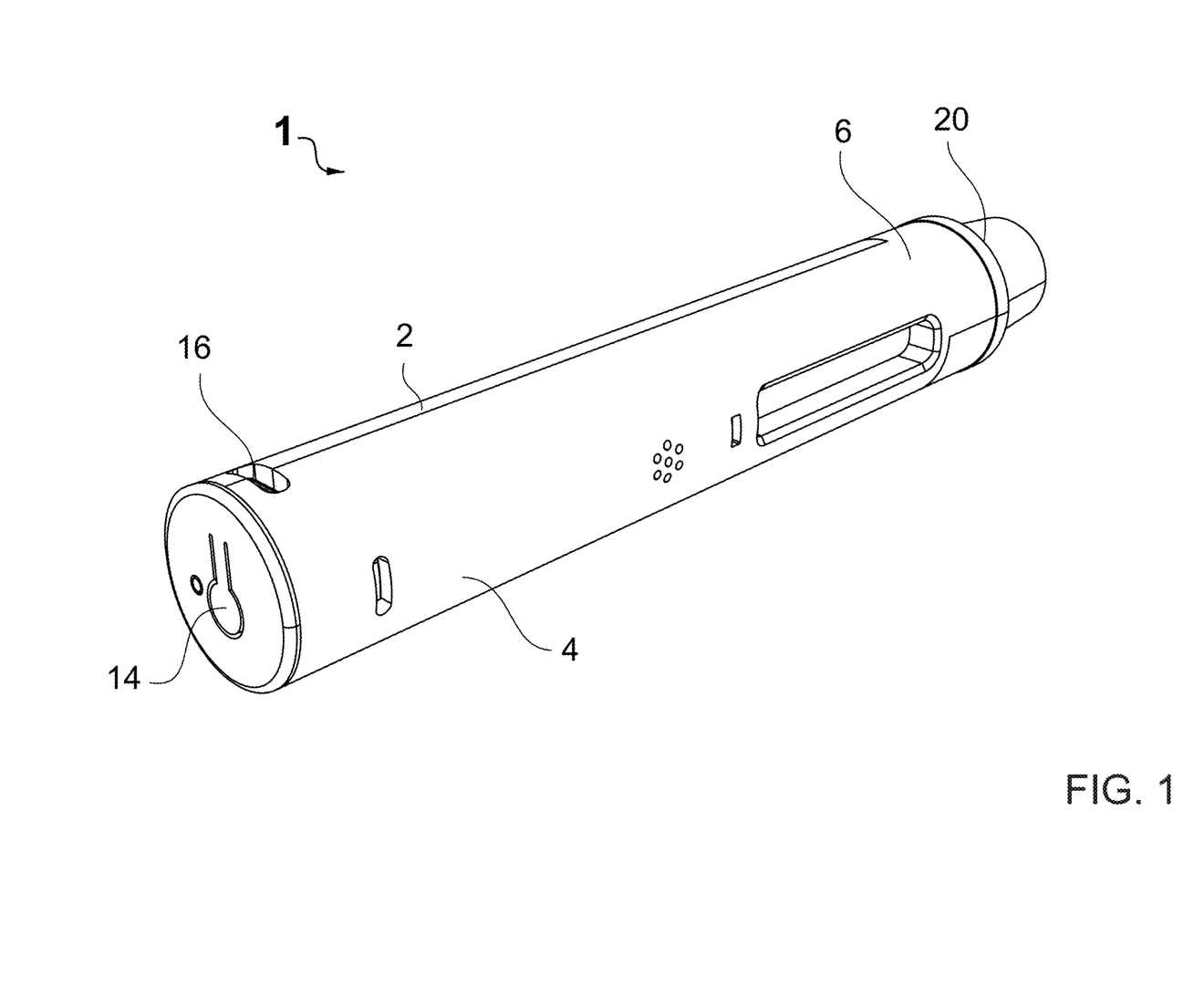
FIG. 1 is a front perspective view of the present invention.
Figure 2:
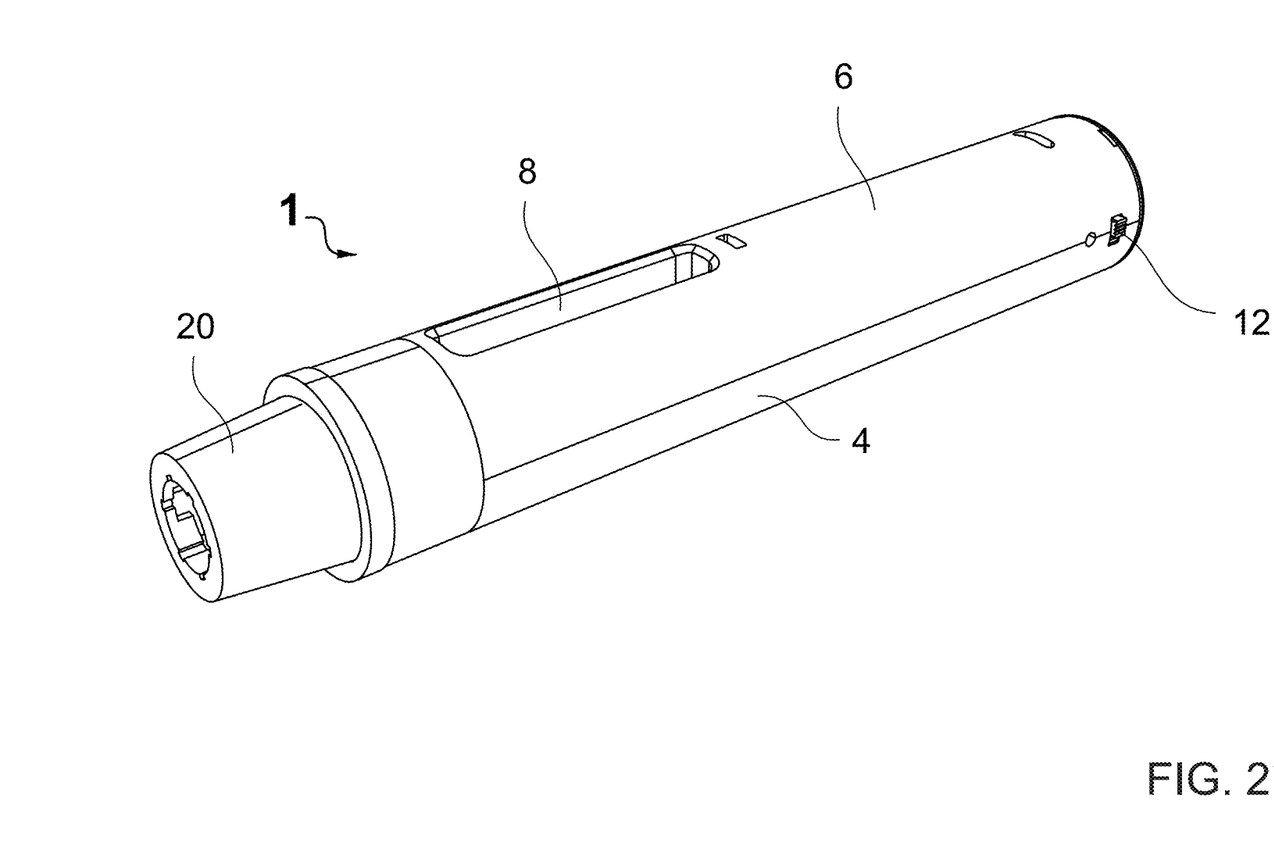
FIG. 2 is a rear perspective view of the present invention.
Figure 3:
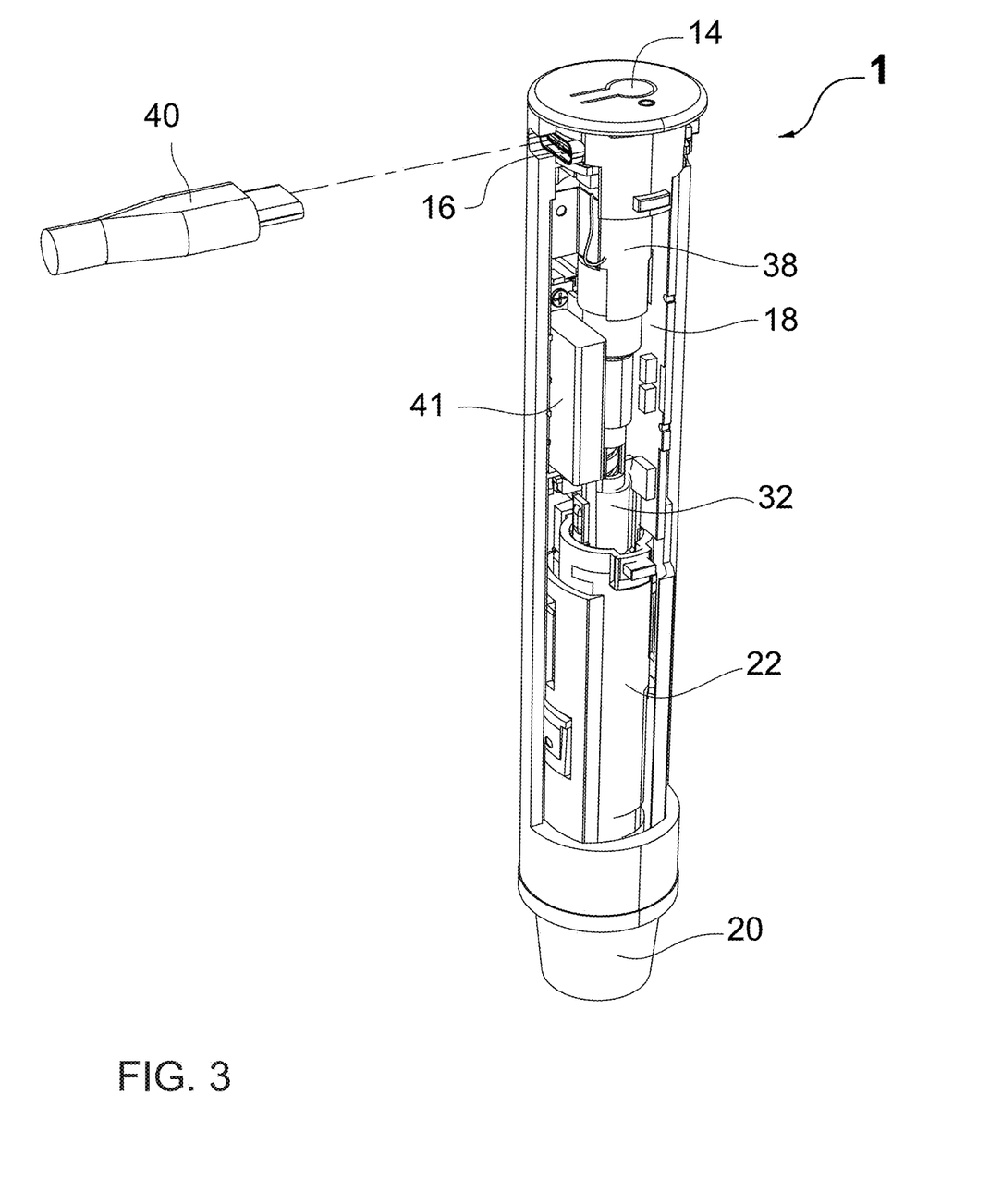
FIG. 3 is a partial sectional front view of the present invention.
Figure 4:
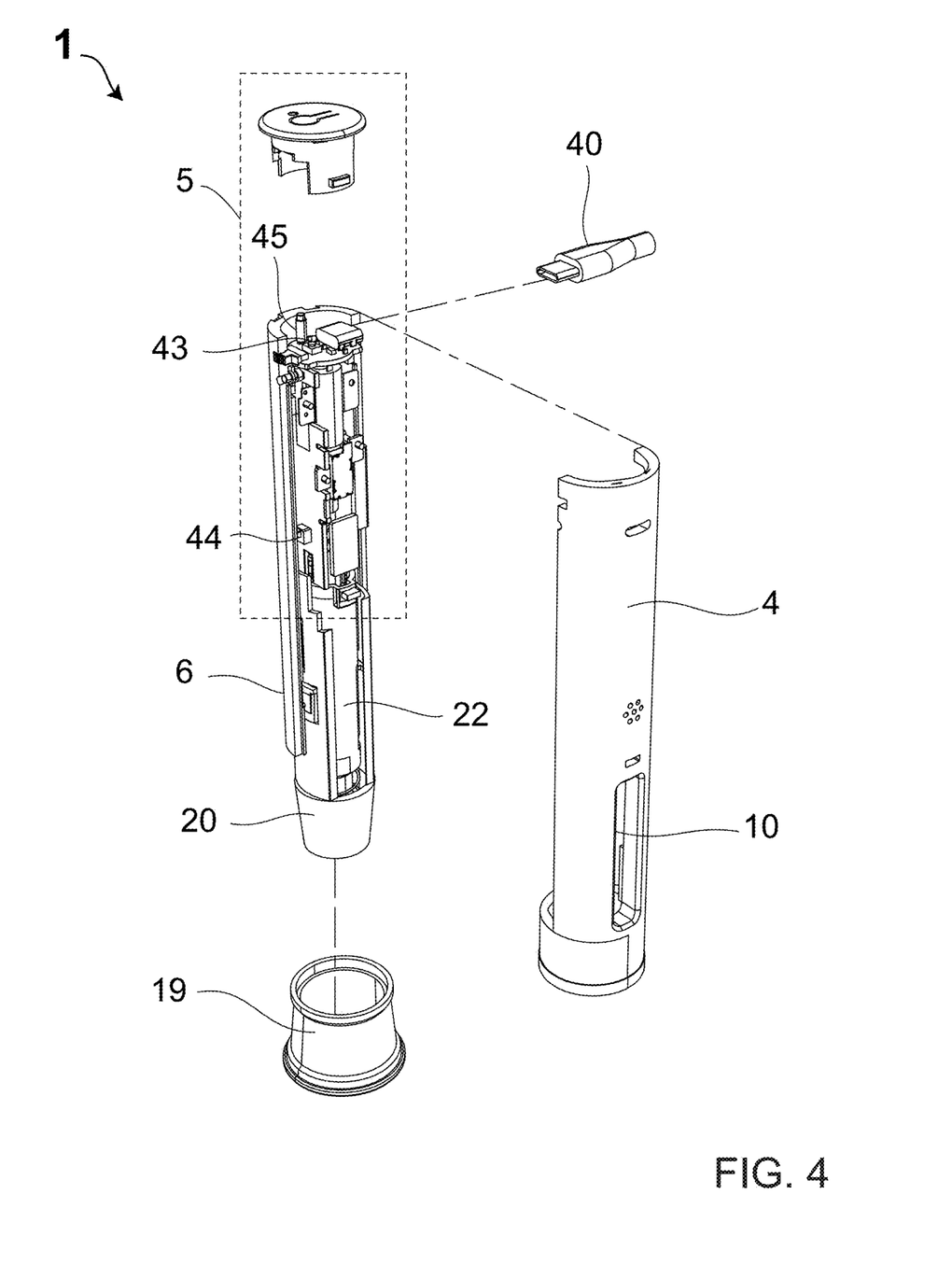
FIG. 4 is an exploded view showing certain components of the present invention.
Figure 5:
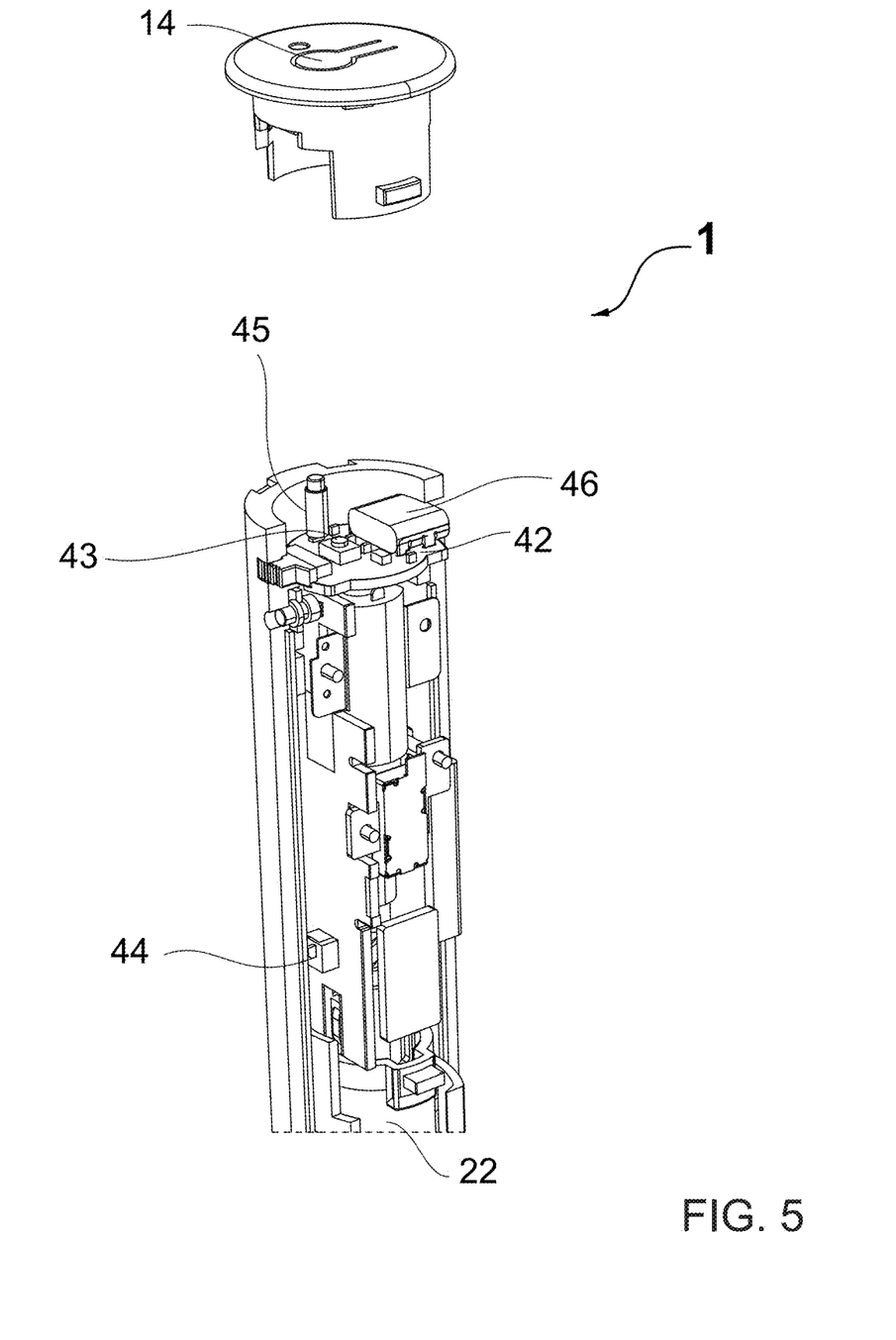
FIG. 5 is a close-up view of the present invention taken from FIG. 4.
Figure 6:
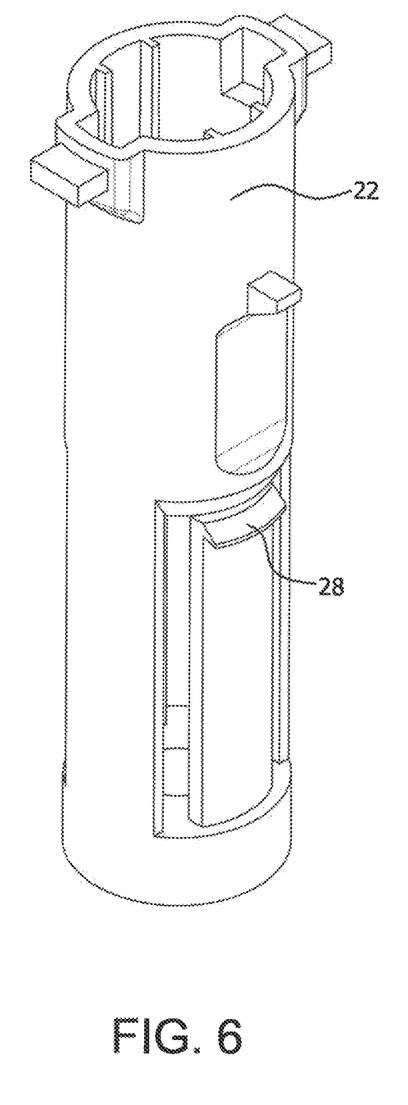
FIG. 6 is a perspective view of the window member of the present invention.
Figure 7:
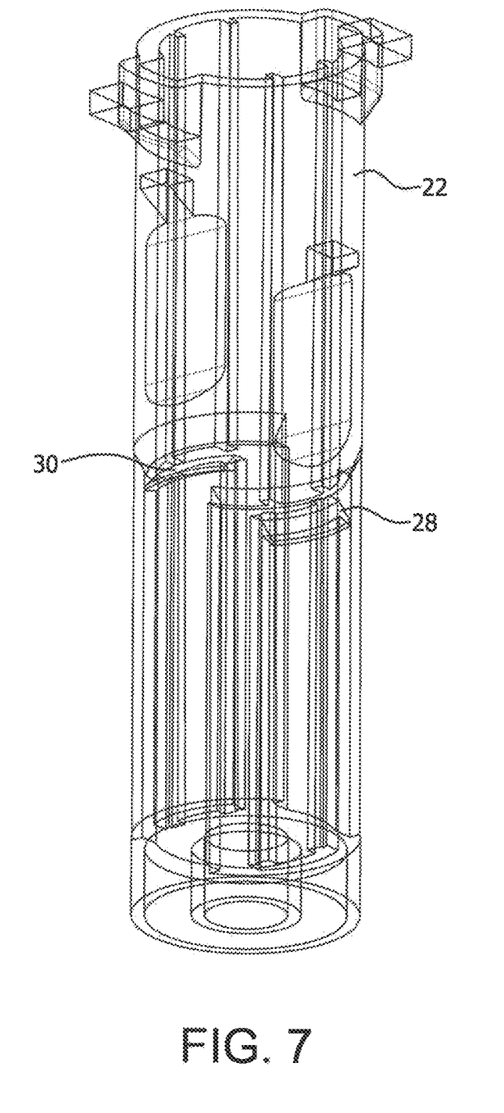
FIG. 7 is a perspective view showing the transparent nature of the window member of the present invention.

Bottom case 4 and top case 6 enclose open space 18 in which various key components of device 1 are positioned. These components include needle guard member 20 and transparent window member 22 located within the needle guard member. With particular reference to FIG. 7, needle guard member 20 has locking slots 24 and 26 extending through its side. Window member 22 has laterally extending stop elements 28 and 30.

Plunger 32 extends into and is movable within window member 22. Plunger 32 has external bump-out elements 34 and 36. Electrical transmission motor 38 is connected to plunger 32 for moving the plunger through window member 22. Motor 38 is powered by battery 41 and is electrically charged by means of charger 40 through charging port 16.

Figure 8:
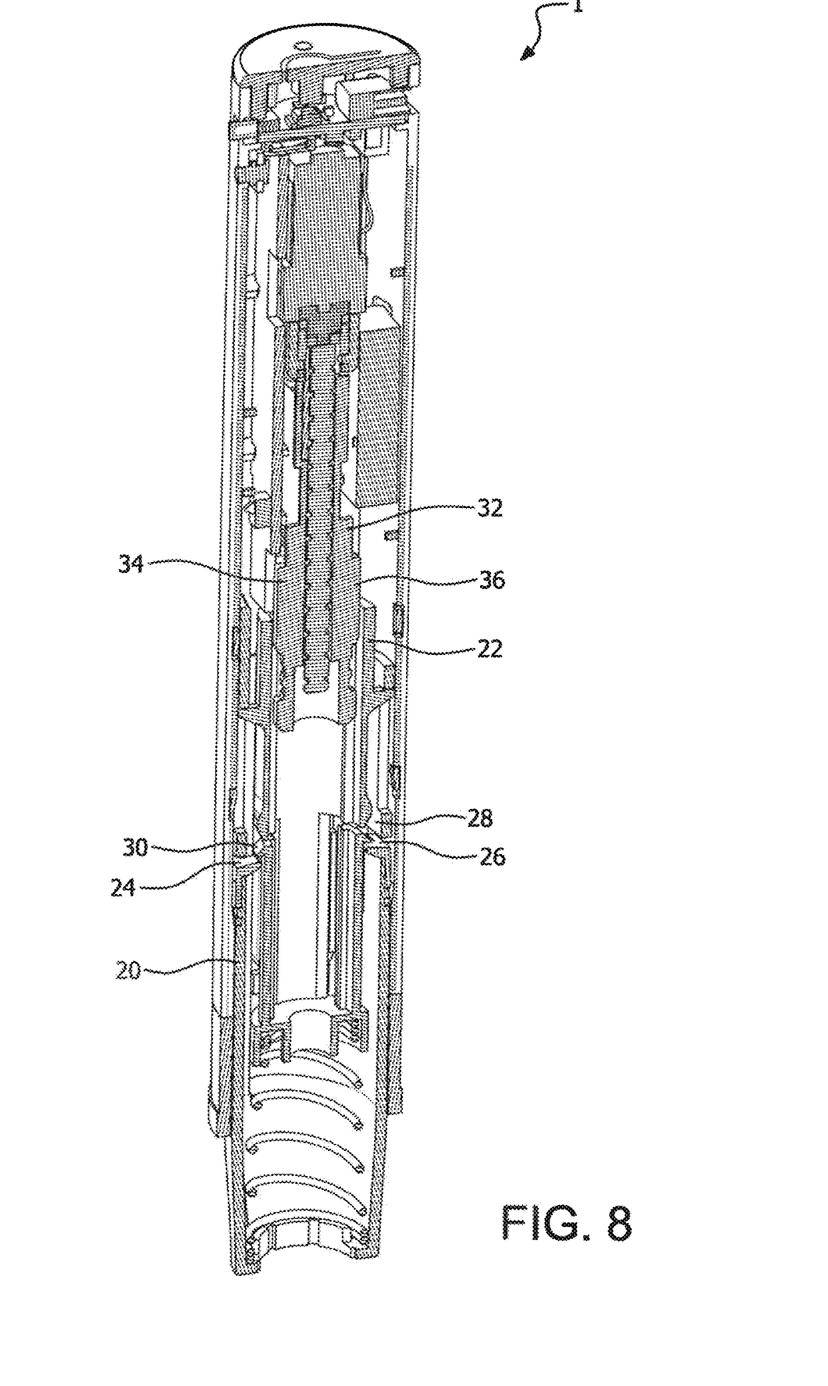
FIG. 8 is a sectional view of the present invention illustrating the position of certain components before injection into the injection site.
Figure 9:
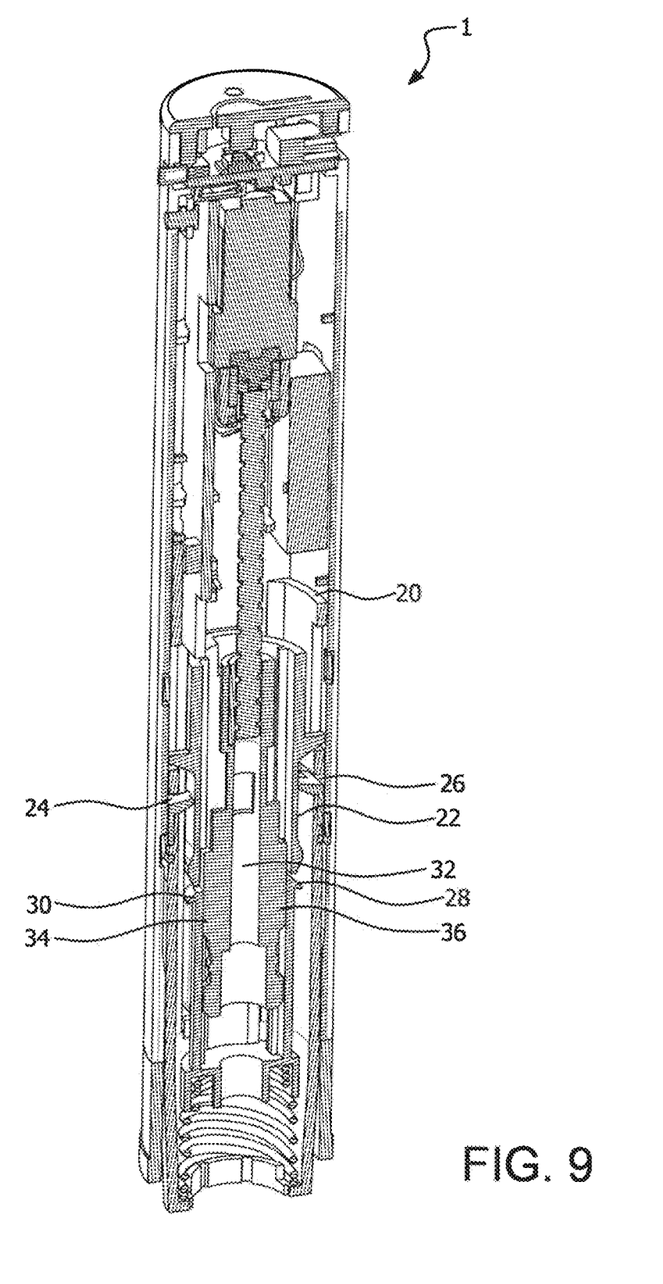
FIG. 9 is a sectional view of the present invention, illustrating the position of certain components during injection into the injection site.
Figure 10:
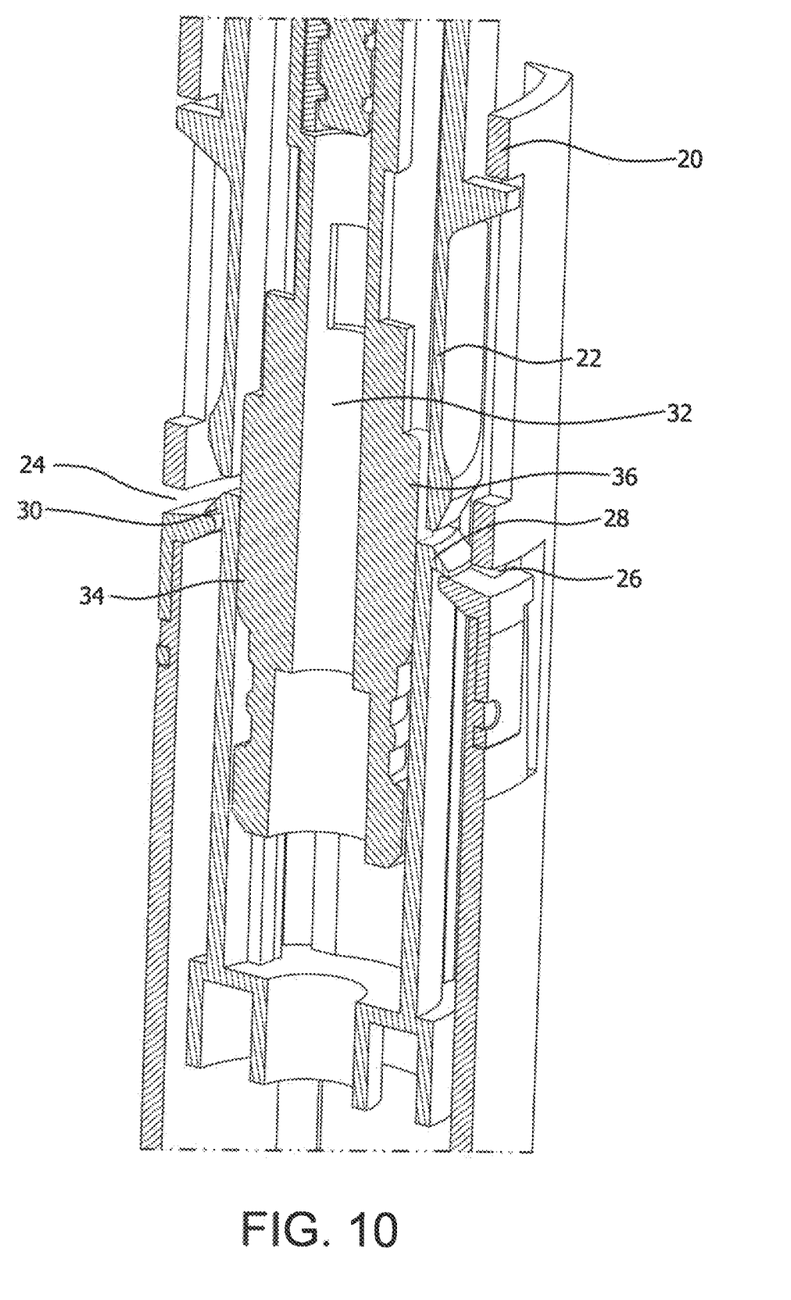
FIG. 10 is a close-up view of the needle guard member of the present invention in its locked position.

With specific reference to FIGS. 8-10, the operation of auto-injector demonstration device 1, to simulate the delivery of medication is as follows:

The user, typically a healthcare provider, first charges the demonstration device's battery 41 by plugging charger 40 into USB-C port 16. The charging LED indicator 45 will be lit until fully charged, when it will go off. The user turns power switch 12 to the "On" position and picks and angles the device to be perpendicular (90 degrees) to the simulated injection site-skin or synthetic skin-chosen for training. (FIG. 8)

Next, the user presses needle guard member 20 against the simulated injection site and applies force until the needle guard member compresses inside window member 22. Once needle guard member 20 reaches its fully compressed position, slide switch 44 connected to an adjacent printed circuit board, will be pressed down by the tip of the needle guard member, enabling software on a central processing unit (CPU) mounted on the PCB to instruct transmission motor 38 to begin to move plunger 32 through the window member 22 at the desired rate of speed for the desired rotation to move the plunger in its simulated medication delivery. (FIG. 9)

When plunger 32 reaches its terminal position, i.e. is fully extended through window member 22, bump-out elements 34 and 36 will compel stop elements 28 and 30 on the window member outward in preparation for achieving locking of needle guard member 20. Once the user allows needle guard member 20 to ease back into that original extended position, protuberant stop elements 28 and 30 will engage with locking slots 24 and 26 through the needle guard member to prevent the needle guard member from retracting into window member 22 (FIG. 10). Needle guard member 20 will stay firmly in this locked/extended position until the user presses reset button 14 in preparation for the next demonstration.

During the reset phase, the user presses reset button 14 located on the top of the device. Tactile switch 43 connected to PCB 42 will notify transmission motor 38 to begin to rotate backward. Plunger 32 will keep moving backward until it presses down on an inner slide switch located behind slide switch 44. When the inner slide switch is pressed, transmission motor 38 will immediately stop rotating and previously protuberant stop elements 28 and 30 will return to their original position. Hence, stop elements 28 and 30 will no longer interact with locking slots 24 and 26 and needle guard member 20 will be free to move again.

To signal key aspects such as the beginning and end of this simulated medication delivery, desirable pre-recorded audio messages will be delivered by an external piezoelectric speaker controlled by software running on a speech IC on the PCBs. In particular, by holding down reset button 14 for at least two seconds, device 1 will access the memory in the Central Processing Unit on the Printed Circuit Board and report the total number of lifetime demonstration cycles (similar to the manner in which a vehicle odometer works) through to the external piezoelectric speaker, which will report the information using a pre-recorded human voice. This feature is important in order to ensure that device 1 is operating properly and demonstrations remain valid.

The haptic feedback will also be delivered by a vibration motor along with the pre-recorded audio to mimic the commercial device more closely and/or otherwise enhance the training experience.

The auto-injector device described in this application is one of several types of linear/pen type devices. In fact, auto-injectors in use today come in a variety of different configurations. For instance, an adhesive patch auto-injector uses a plunger which moves transversely with respect to its needle's direction. It should be understood that the system and operation of the auto-injector demonstration device disclosed herein has application to and is contemplated for use in auto-injector demonstration devices of different styles, designs, and configurations. As such, the herein disclosure is not to be considered so restricted.

Certain novel features and components of this invention are disclosed in detail in order to make the invention clear in at least one form thereof. However, it is to be clearly understood that the invention as disclosed is not necessarily limited to the exact form and details as disclosed, since it is apparent that various modifications and changes may be made without departing from the spirit of the invention.

The invention claimed is:

1. An auto-injector demonstration device for simulating the delivery of medication into an injection site, said device comprising:
  an elongated injector body;
  a needle guard member located within the injector body;
  a transparent window member having at least one laterally extending stop element, said window member being circumscribed by the needle guard member which is movable within the window member;
  a plunger extending into and movable through the window member and the needle guard member, said plunger having external bump-out elements; and
  an electrical transmission motor for moving the plunger through the window member to simulate the medication delivery, wherein continued movement of the plunger will cause the plunger to be fully extended within the window member, resulting in the at least one stop element of the window member being compelled outward ultimately for achieving locking of the needle guard member.

2. The auto-injector demonstration device as in claim 1 wherein the needle guard member has at least one locking slot into which the at least one stop element engages to retain the needle guard member in a locked position.

3. The auto-injector demonstration device as in claim 1 wherein the injector body has at least one channel opening to allow components of the device to be observed when the device is being used.

4. The auto-injector demonstration device as in claim 2 wherein the needle guard member has two locking slots and the window member has two stop elements, the stop elements of the window member being engaged into the locking slots of the needle guard member to retain the needle guard member in the locked position.

5. The auto-injector demonstration device as in claim 1 wherein a reset button is located on the device to cause the transmission motor to retract from its fully extended position within the window member when the reset button is pressed.

6. The auto-injector demonstration device as in claim 5 wherein upon the reset button being pressed and held, the device reports the total number of lifetime demonstration cycles through an external piezoelectric speaker.

* * * * *